United States Patent [19]

Killig et al.

[11] 4,277,687
[45] Jul. 7, 1981

[54] TOMOGRAPHIC APPARATUS FOR PRODUCING TRANSVERSE LAYER IMAGES

[75] Inventors: Klaus Killig, Hoechstadt; Wolfhart Lichtenberg; Rudolf Schittenhelm, both of Erlangen, all of Fed. Rep. of Germany

[73] Assignee: Siemens Aktiengesellschaft, Berlin & Munich, Fed. Rep. of Germany

[21] Appl. No.: 86,064

[22] Filed: Oct. 18, 1979

[30] Foreign Application Priority Data

Nov. 22, 1978 [DE] Fed. Rep. of Germany ....... 2850675

[51] Int. Cl.³ .............................................. G03B 41/16
[52] U.S. Cl. .................................. 250/445 T; 250/505
[58] Field of Search ................... 250/445 T, 505, 514, 250/515

[56] References Cited

U.S. PATENT DOCUMENTS 4,128,781  12/1978  Flisikowski ..................... 250/445 T 4,150,293  4/1979  Franke ............................. 250/445 T

OTHER PUBLICATIONS

"Computerized Tomographic Scanner," American Science and Engineering, ASE-3269, Apr. 1976.

Primary Examiner—Craig E. Church
Attorney, Agent, or Firm—Hill, Van Santen, Steadman, Chiara & Simpson

[57] ABSTRACT

In the exemplary embodiments, a radiation measuring arrangement which includes radiation source is rotated for irradiating the radiography subject from different directions. A measured value converter calculates a layer image from the output signals of the detectors of the radiation receiver. For shielding against stray radiation, two hollow cylinders of equal diameter and with a common axis and comprised of a radiation-absorbing material lie between the radiation source and the radiation receiver, a gap for the passage of the x-ray beam being left therebetween. The radiography subject is introduced into the hollow cylinders.

3 Claims, 4 Drawing Figures

TOMOGRAPHIC APPARATUS FOR PRODUCING TRANSVERSE LAYER IMAGES

The invention relates to a tomograph for producing transverse layer images of a radiography subject, having a radiation measuring arrangement which contains both a radiation source producing a beam of rays which penetrates the radiography subject and whose cross sectional extent perpendicular to the layer plane is equal to the layer thickness, and a radiation receiver which determines the radiation intensity behind the object, and also having a rotating arrangement for the measuring arrangement for irradiating the radiography subject from different directions and having a measured value converter for transforming the signals supplied by the radiation receiver into a layer image.

In a tomograph of this kind, a so-called computer tomograph, the attenuation values of specific points in the irradiated layer are calculated from the output signals of the radiation receiver, which are produced at different projections, and reproduced as an image of this layer. Measuring the radiation attenuation correctly is made more difficult in this connection by the occurrence of scattered radiation. The proportion of scattered radiation which is registered together with the attenuated primary radiation may be reduced by a collimator system arranged before the radiation receiver with a three-dimensional angle (solid angle) of aperture which is as small as possible to allow only radiation from the focus and its vicinity to be transmitted.

In computer-tomographs with a radiation receiver consisting of a row of detectors which, together with the radiation source, is rotated about the radiography subject, a leaf collimator is generally arranged before the detectors of the radiation receiver and aligned on to the focus. Its action is explained in more detail with reference to FIG. 1. The action of the collimator is based on the fact that all but a fraction of the surface of the patient emitting scattered radiation for the detectors is masked.

In another type of computer-tomograph shown in FIG. 2 an x-ray tube is rotated by 360° about the patient, and the radiation receiver is formed by a stationary ring of detectors which encloses the patient and the circular path of the x-ray tube. In this type of computer tomograph each detector must be able to detect the two peripheral rays whose paths lie outside the patient 5 so that it is not possible to suppress the scattered radiation by collimation in the layer plane.

SUMMARY OF THE INVENTION

The underlying object of the invention is to construct a tomograph of the initially named type so that the scattered radiation is suppressed in every case, i.e. also when a stationary ring of detectors is used as the radiation receiver.

This object is achieved according to the invention by placing between the radiation source and the radiation receiver two hollow cylinders made of a radiation-absorbing material and having equal diameters and a common axis, a clearance being left between them for the passage of the x-ray beam and into which the radiography subject can be introduced. In the case of the tomograph according to the invention, the two hollow cylinders form a ring collimator which suppresses the scattered radiation in the longitudinal direction of the patient. It is thus applicable for all types of computer tomographs.

The invention is explained in more detail in the following with reference to exemplary embodiments represented in FIGS. 3 and 4 showing two views of a tomograph according to the invention; and other objects, features and advantages will be apparent from this detailed disclosure and from the appended claims.

DETAILED DESCRIPTION

Figure 1:
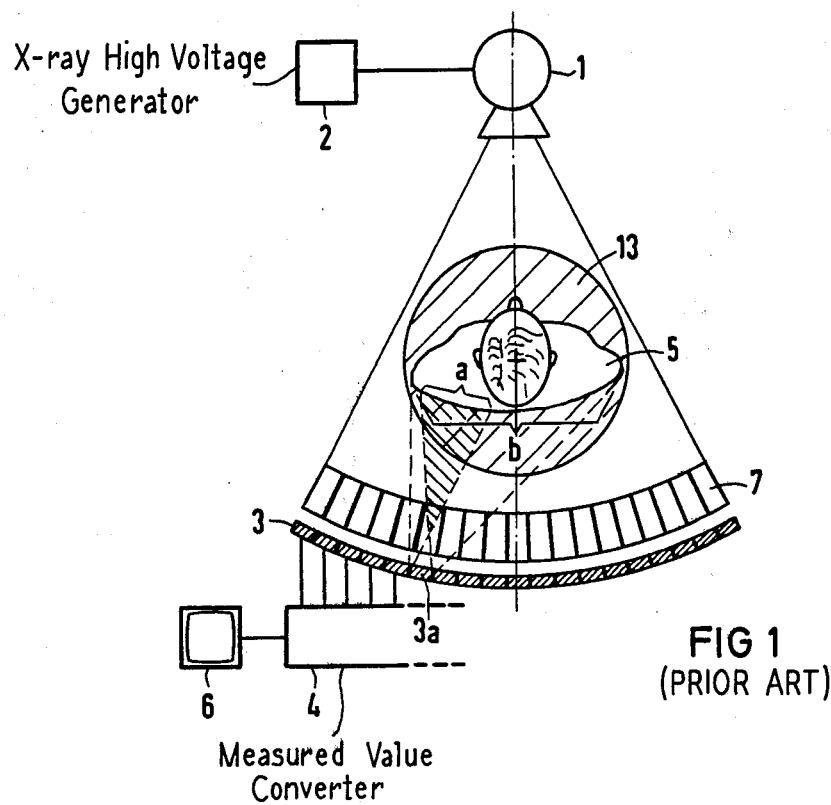
FIG. 1 is a diagrammatic vertical sectional view of a first form of known tomographic apparatus to which the present invention is applicable.

In computer-tomographs with a radiation receiver consisting of a row of detectors which, together with the radiation source, is rotated about the radiography subject, a leaf collimator is generally arranged before the detectors of the radiation receiver and aligned on to the focus. Its action is explained in more detail with reference to FIG. 1. FIG. 1 shows an x-ray tube 1 as the radiation source, which is fed by an x-ray high voltage generator 2 and also a radiation receiver 3 which consists of a row of individual detectors, for example 256 detectors. Each detector is linked with a computer 4 which calculates an image of the irradiated cross section of the patient 5 from the output signals of the detectors of the radiation receiver 3 and reproduces this image on a monitor 6.

Arranged before the radiation receiver 3 is a leaf collimator 7 whose leaves are aligned on to the focus of the x-ray tube 1. The action of the collimator 7 is based on the fact that all but a fraction of the surface of the patient emitting scattered radiation for the detectors is masked. Thus, for example for the detector 3a only the surface section a is decisive for detecting scattered radiation, whereas without the collimator, the entire surface b of the patient is effective.

Figure 2:
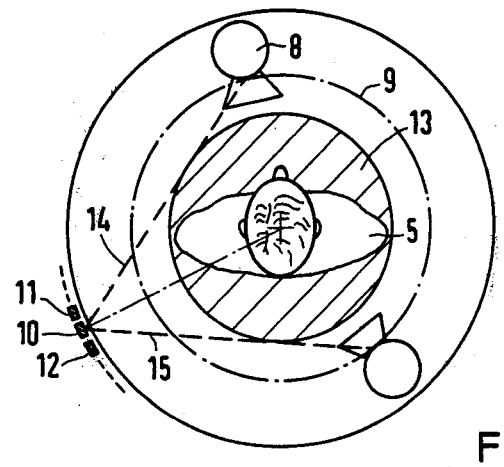
FIG. 2 is a diagrammatic vertical sectional view showing a second type of tomographic apparatus to which the present invention may be applied.

FIG. 2 shows a computer-tomograph in which an x-ray tube 8 with its focus on a circle 9 is rotated by 360° around the patient 5, and wherein the radiation receiver is formed by a ring of detectors which encloses the patient 5 and the x-ray tube 8. Only three detectors 10, 11, 12 from this ring of detectors are drawn in FIG. 2. In this type of computer tomograph each detector must be able to detect the two peripheral rays of the measuring field 13. These two peripheral rays are designated by 14 and 15 for the detector 10. The paths of these peripheral rays lie outside the patient 5 so that it is not possible to suppress the scattered radiation by collimation in the layer plane.

Figure 3:
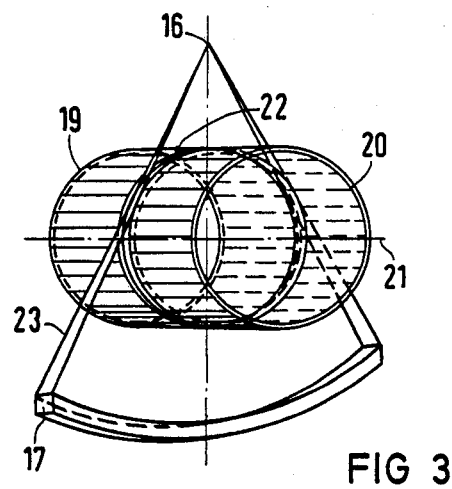
FIG. 3 is a diagrammatic perspective view which may be taken as illustrating an embodiment of the present invention applied to the apparatus of FIG. 1 but where a gap between stationary collimator cylinders is of constant width over its entire 360° extent.
Figure 4:
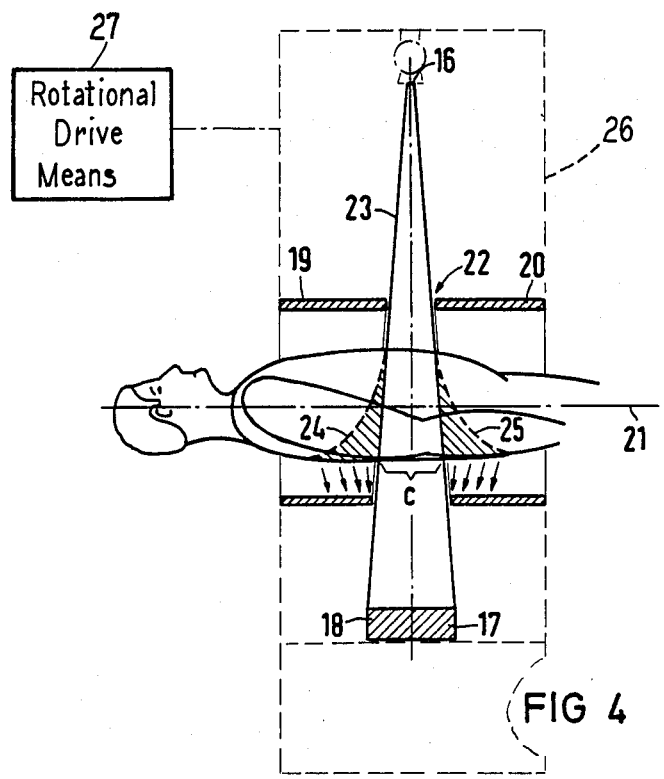
FIG. 4 is a diagrammatic longitudinal sectional view showing an arrangement somewhat similar to FIG. 3 and applied to the apparatus of FIG. 1, but with the collimator cylinders mechanically connected with the rotating frame which carries the x-ray source, the gap between the cylinders accommodating a laterally extensive fan-shaped beam as shown in FIG. 3, and allowing the beam to progressively increase in its longitudinal extent as a function of distance from the x-ray tube focus, but being of a minimum width at its side facing the focus and of an increased width at the side remote from the focus so as to conform to the direct diverging beam path between the focus and the radiation receiver as closely as possible at each point.

The tomograph according to FIGS. 3 and 4 is a tomograph having rotation exclusively of the measuring arrangement and using a row of detectors as the radiation receiver, as shown in priciple in FIG. 1. Only the focus 16 of the x-ray tube is shown in FIGS. 3 and 4. The radiation receiver is designated by 17. In the sectional representation according to FIG. 4, one detector 18 of the radiation receiver 17 is represented.

Between the focus 16 and the radiation receiver 17 there are two hollow cylinders 19, 29 forming a collimator with equal diameters and a common axis which coincides with the axis of rotation 21 of the unit. The hollow cylinders 19, 20 consist of radiation-absorbing material. A narrow gap 22 is left between them for the passage of the fan-shaped beam of x-rays 23. The radiography subject, i.e. the patient, is introduced into the hollow cylinders 19, 20, as shown in FIG. 4. It can be seen from FIG. 4 that most of the scattered radiation occurring in the patient in the zones 24, 25 is absorbed for the most part by the hollow cylinders 19, 20 in the direction of the axis of rotation 21. The detector 18 detects only that scattered radiation issuing from the patient in the narrow surface region c.

There are two possibilities for the construction of the hollow cylinders 19, 20. If, when the measuring arrangement rotates, the hollow cylinders 19, 20 rotate with them with the same angular velocity, the gap 22 may, as illustrated in FIG. 4, be dimensioned so that the breadth of the gap is smaller on the side where the radiation enters than on the side where the radiation leaves, so that a beam of rays 23 converging to the focus is collimated by the gap. In this case, the gap 22 therefore is adapted to the cross section of the layer. If, when the measuring arrangement rotates, the hollow cylinders 19, 20 remain stationary, the breadth of the gap must be constant over the entire periphery. The rays defining the layer are thus restricted by the two confronting edge faces of the cylinders on the exit side for the rays, i.e. only at the side of the cylinder peripheries remote from the position of focus 16.

The invention is applicable quite generally to all types of computer tomographs, i.e. to computer tomographs in which an alternate rotation and lateral displacement of the radiation receiver and a narrow beam of rays takes place, to computer tomographs in which the fan radiation method with a rotating detector system according to FIG. 1 is used, to computer tomographs which operate in accordance with FIG. 2 according to the fan radiation method and have a stationary ring of detectors and also to computer tomographs in which the fan radiation method is applied using several x-ray sources with a corotating or stationary radiation receiver.

For the sake of specific diagrammatic illustration, FIG. 4 may be taken as showing an x-ray tube-detector arrangement according to FIGS. 1 and 3 wherein the x-ray tube with focus 16 and the associated arcuate arrangement 17 of detectors such as 18 is rotated about axis 21. The hollow cylinders 19-20 may be physically secured with the rotary frame indicated at 26 so as to be driven for rotation about axis 21 by the rotational drive means indicated at 27 along with the x-ray source 16 and detector arrangement 17. The collimator 7 for providing lateral collimation as shown in FIG. 1 may form part of the rotary detector arrangement 17 of FIG. 4.

It will be apparent that many modifications and variations may be effected without departing from the scope of the novel concepts and teachings of the present invention.

We claim as our invention:

1. A tomographic apparatus for producing transverse layer images of a radiography subject, having a radiation measuring arrangement which contains both a radiation source producing a beam of rays which penetrates the radiography subject and whose cross sectional extent perpendicular to the layer plane is equal to the layer thickness, and a radiation receiver which determines the radiation intensity behind the subject, and also having means for producing rotational displacement of the beam of rays for irradiating the radiography subject from different directions, and having a measured value converter for transforming the signals supplied by the radiation receiver into a layer image, characterized in that two hollow cylinders (19, 20) are disposed between the radiation source (16) and the radiation receiver (17) and into which the radiography subject may be introduced, said cylinders (19, 20) having substantially the same diameter, having substantially a common axis (21) and being comprised of a radiation-absorbing material except at a gap (22) therebetween left free for the passage of the x-ray beam (23).

2. A tomographic apparatus according to claim 1, characterized in that the hollow cylinders (19, 20) remain stationary during rotational displacement of the beam of rays, and in that the width of the gap is constant over the entire periphery so that the rays defining the layer are restricted by gap-defining faces of the cylinders at the exit side for the rays.

3. A tomographic apparatus according to claim 1, characterized in that, the hollow cylinders (19, 20) are corotated with the same angular velocity during rotational displacement of the beam of rays and in that the width of the gap (22) is smaller at the input side for the rays than at the output side for the rays so that a beam of rays (23) converging to the radiation source (16) is collimated by the gap (22).

* * * * *